United States Patent [19]
DiSabito

[11] Patent Number: 5,261,402
[45] Date of Patent: Nov. 16, 1993

[54] SNAPLESS, TABLESS, DISPOSABLE MEDICAL ELECTRODE WITH LOW PROFILE

[75] Inventor: David M. DiSabito, Clarence, N.Y.

[73] Assignee: Graphic Controls Corporation, Buffalo, N.Y.

[21] Appl. No.: 916,545

[22] Filed: Jul. 20, 1992

[51] Int. Cl.$^5$ ............................................. A61B 5/04
[52] U.S. Cl. ..................................... 128/640; 128/641
[58] Field of Search ............... 128/639, 640, 641, 802, 128/803

[56] References Cited

U.S. PATENT DOCUMENTS

| | | | |
|---|---|---|---|
| 3,599,629 | 8/1971 | Gordy | 128/640 |
| 3,788,317 | 1/1974 | McCormick | 128/641 |
| 4,102,331 | 7/1978 | Grayzel et al. | 128/640 |
| 4,311,152 | 1/1982 | Modes et al. | |
| 4,490,005 | 12/1984 | Hovey . | |
| 4,498,480 | 2/1985 | Mortensen . | |
| 4,515,162 | 5/1985 | Yamamoto et al. | |
| 4,635,642 | 1/1987 | Cartmell et al. | |
| 4,674,512 | 6/1987 | Rolf . | |
| 4,699,679 | 10/1987 | Cartmell et al. | |
| 4,798,208 | 1/1989 | Faasse, Jr. . | |
| 4,809,699 | 3/1989 | Shimizu et al. | |
| 4,827,939 | 5/1989 | Cartmell et al. | |
| 4,848,351 | 7/1989 | Finch . | |
| 4,848,353 | 7/1989 | Engel . | |
| 4,911,657 | 3/1990 | Berlin . | |
| 5,042,498 | 8/1991 | Dukes . | |

OTHER PUBLICATIONS

Sentry Medical Products of 17171 Murphy Avenue, Irvine, Calif. 92714; have advertised an $SS_2$ Electrode System: a copy of the advertisment (dated Apr. 1991) is provided.
The Minnesota Mining & Manufacturing Co. of St. Paul Minn. has advertised a Red Dot TM Cardiac Sensor. System A copy of the Advertisement (dated Feb. 1991) is provided.

*Primary Examiner*—Lee S. Cohen
*Attorney, Agent, or Firm*—Ratner & Prestia

[57] ABSTRACT

A snapless, tabless, disposable medical electrode having a low profile for transmitting electrical signals between the skin of a patient and external monitoring equipment. The electrode has an adhesive substrate with a central opening and a pressure sensitive adhesive layer on its bottom (which faces the patient); a symmetrical, electrically conductive disk secured to the substrate, formed without a tab and without a snap, and positioned over and projecting above the central opening of the substrate; a conductive medium substantially filling the opening of the substrate and electrically contacting the skin of the patient, the substrate, and the disk; a lead wire, attached to the disk without regard to orientation, for connecting the disk to the external monitoring equipment; and a release liner covering the bottom of the substrate and gel before the electrode is secured to the skin of the patient.

21 Claims, 4 Drawing Sheets

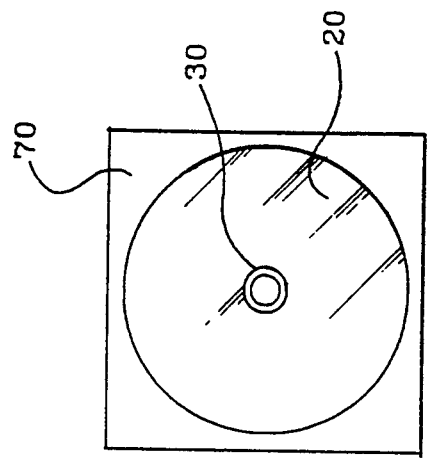
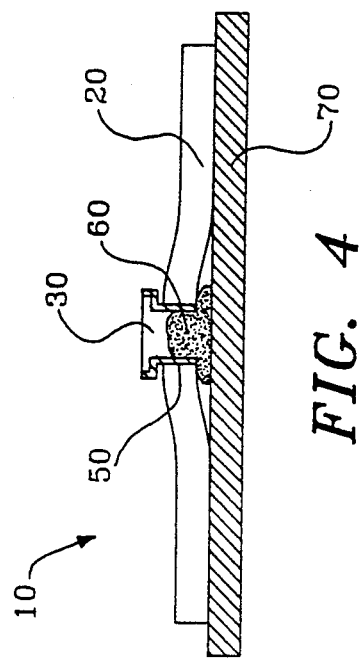
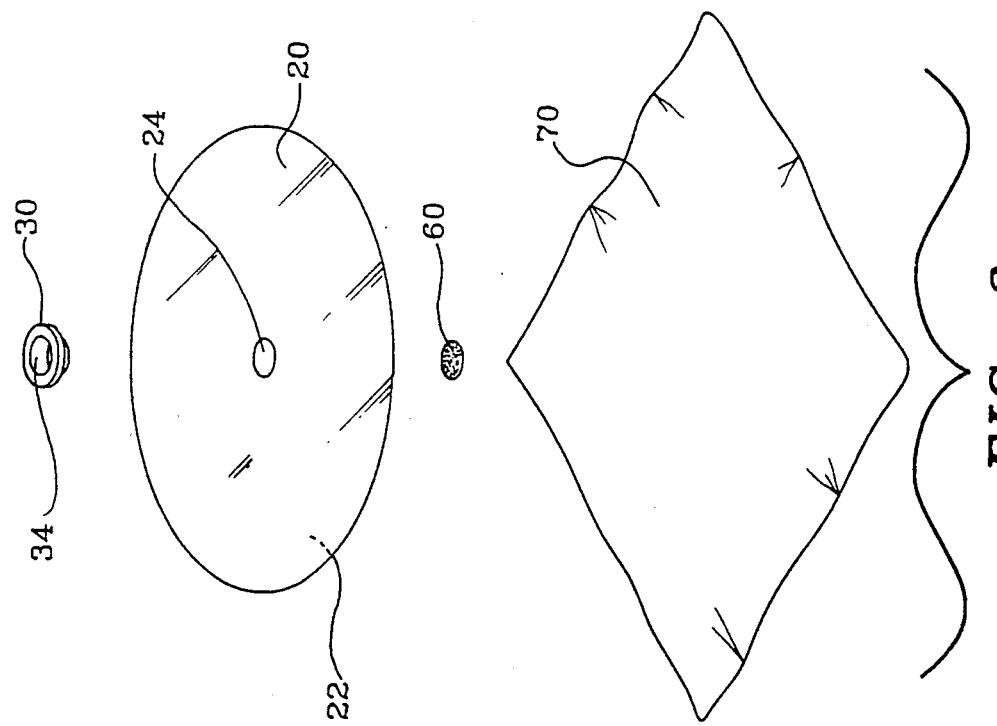

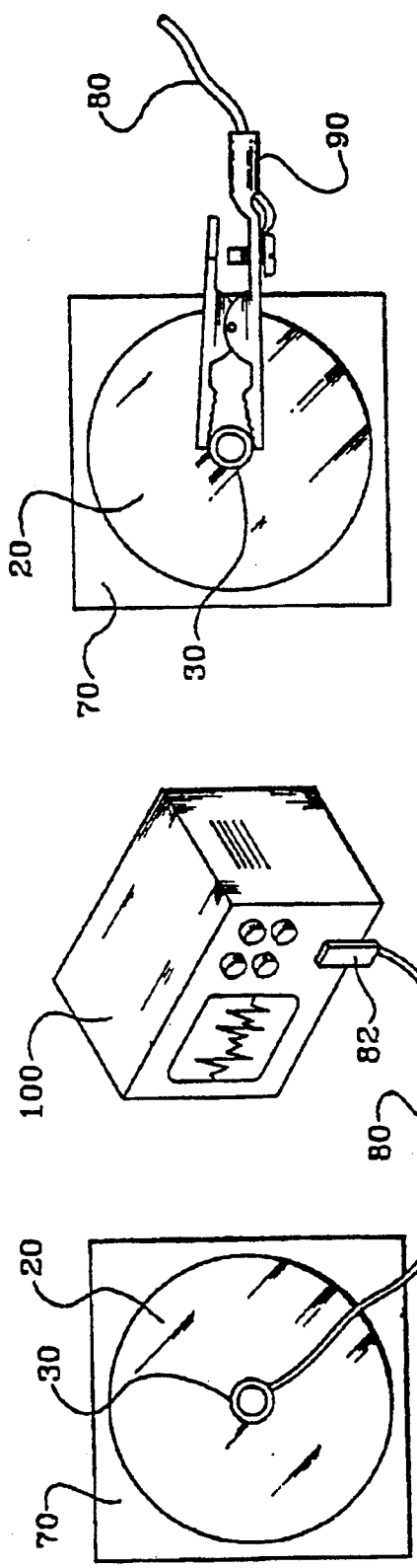
FIG. 7
FIG. 6
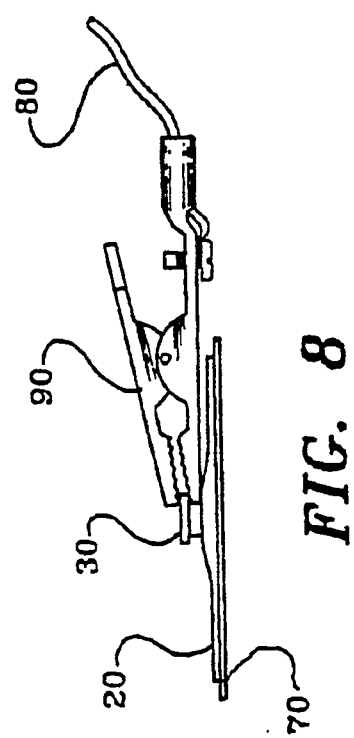
FIG. 8

SNAPLESS, TABLESS, DISPOSABLE MEDICAL ELECTRODE WITH LOW PROFILE

FIELD OF THE INVENTION

The present invention relates to a biomedical electrode of the type attached to the body and, more particularly, to a snapless, tabless, disposable medical electrode having a low profile for transmitting electrical signals between the skin of a patient and peripheral monitoring equipment.

BACKGROUND OF THE INVENTION

Medical electrodes are well known in the art and vary considerably in their structure and configuration. They generally have a substrate designed to be applied and held to the skin of a patient, an electrical connector, and a conductive lead wire removably and electrically attached to the electrical connector on one end and to a monitoring device on its opposite end. The field is relatively crowded.

Designs are usually controlled by, first, a requirement for a secure fastening of the electrical connector to the skin because the electrode may be part of a life support system. A second requirement of an electrode design is controlled by economics. There is a continuing need for high quality but inexpensive medical electrodes. For purposes of convenience and safety (e.g., to maintain sterility in a medical environment), the electrode should be sufficiently inexpensive to manufacture that it is practical to dispose of and to replace the electrode after only one use (hence, the electrode must be "disposable").

The various medical electrode designs can generally be placed into two categories. In one category are snap-type electrodes in which one end of the electrical connector terminates in a projecting snap or stud. The lead wire is provided with a mating eyelet or socket which receives and secures, by snapping over, the snap. An advantage of such an electrode is that it permits rotation between the electrode and the lead wire. Rotation assures patient comfort, prevents the electrode from disengaging when the patient moves, and allows connection between the lead wire and electrical connector without regard to orientation.

It is common to form the projecting snap from a non-conducting substrate and then to coat that substrate with a very thin coating of a conductive material. The thin coating of conducting material is easily abraded away, however, when the outer wall of the snap frictionally contacts and slides against the eyelet, as happens when the snap electrode rotates with respect to its lead wire. The resulting abrasion of the mating surfaces of the snap and eyelet can eventually degrade the electrical conductivity between the electrode and the lead wire.

To minimize the rotation between the electrode and lead, and the consequent degradation, some electrodes prevent relative rotation. Such electrodes restrict the versatility and ease of manipulation for the electrode, as well as the equipment to which the electrode is connected.

Another problem with the snap-type electrodes is that they have a relatively high profile (height). The snap must project from the electrode a significant distance to allow connection of the lead wire eyelet. A high profile is disadvantageous because it makes the electrode more noticeable and increases the risk of damage by hitting other objects during use and storage. The electrical contacts between the snap and the lead wire eyelet and between the electrode and the patient are essential; those contacts must be protected from disengagement. Consequently, a low profile electrode is preferable.

The second type of electrode has no projecting snap or stud. It is usually thin, flat, flexible, disposable, snapless, and, therefore, substantially less expensive to manufacture or use. The lead wire interconnects the second type of electrode by engaging the electrode itself, usually at a lateral extension or tab at one side or at the center of the electrode. Thus, this second type of electrode is referred to as a "tab" electrode.

One problem with the tab electrode is that it typically does not permit rotation between the electrode and the lead wire. A particular orientation of the lead wire with respect to the tab of the electrode is required. Another problem is that tab electrodes generally are connected to their lead wires by spring or alligator clips affixed to the tab. Such clips typically give the clip-electrode combination a high profile. Moreover, the clips occasionally slip off the tab, rip through the tab, or tear the tab away from the remainder of the electrode and, therefore, are not entirely satisfactory under certain circumstances.

Regardless of the design, both snap-type and tab-type conventional medical electrodes are relatively complex in their structure. Many of these electrodes have hard, bulky components which make them uncomfortable to the patient. Most suffer from motion artifacts.

Motion artifacts can be defined as motion-induced fluctuation of skin potential. Such artifacts create electrical interference which is often superimposed on the bipotential skin signal measured by the electrode, thereby reducing the electrode's usefulness as a diagnostic and clinical tool. Motion artifacts have long been a problem in measuring biopotentials, particularly in long-term electrocardiogram (ECG or EKG) monitoring of coronary care patients and in exercise (stress) ECG's.

Artifacts are generally caused by movement of the patient (who may be on a moving treadmill, for example, to induce increased heart and respiratory rates) relative to the electrode applied to the patient's skin. That movement disturbs the skin potential and creates extraneous output on the monitor which either masks the desired bipotential signal or shifts the base line.

As the above discussion makes evident, the problem of providing a highly reliable, disposable, low profile electrode has presented a major challenge to designers in the health care field. The development of an economical, tabless (so orientation is eliminated) medical electrode would represent a major technological advance in the field. The advantages of such a device would satisfy a long-felt need within the medical profession.

Therefore, to overcome the shortcomings of the existing medical electrodes and to satisfy the need of the medical profession, a new, snapless, tabless, disposable medical electrode is provided. A primary object of the present invention is to provide an improved medical electrode which can be manufactured at low cost yet meets the structural requirements of the market. A related object is to provide an electrode which is economical and simple in design, yet durable and highly effective to use.

Patient comfort is an overriding concern with any electrode design. Accordingly, it is an object of the present invention to assure patient comfort. At the same time, rotational movement between the lead wire and electrode may be necessary to provide a good electrical connection. Such connection must be assured even when the patient moves. Accordingly, it is another object of the present invention to assure significant rotational movement between the lead wire and the electrode. It is still another object of the present invention to reduce motion artifacts.

An additional object is to assure that the electrode has a very low profile. Yet another object of this invention is to allow for quick and easy attachment and detachment, both to and from the patient and between the electrode and its lead wire, without concern for a specific orientation. Both types of attachment and detachment should be sufficiently simple that they can be done in the dark.

SUMMARY OF THE INVENTION

To achieve these and other objects, and in view of its purposes, the present invention provides a snapless, tabless, disposable medical electrode having a low profile for transmitting electrical signals between the skin of a patient and external monitoring equipment. The electrode has an adhesive substrate with a central opening and a pressure sensitive adhesive layer on its bottom (which faces the patient); a symmetrical, electrically conductive disk secured to the substrate, formed without a tab and without a snap, and positioned over and projecting above the central opening of the substrate; a conductive medium (e.g., an adhesive, electrolyte gel) substantially filling the opening of the substrate and electrically contacting the skin of the patient, the substrate, and the disk; a lead wire, attached to the disk without regard to orientation, for connecting the disk to the external monitoring equipment; and a release liner covering the bottom of the substrate and gel before the electrode is secured to the skin of the patient.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which:

FIG. 3 is an exploded, perspective view of a snapless, tabless, disposable medical electrode according to a second embodiment of the present invention;

FIG. 4 is a cross-sectional view of the electrode shown in FIG. 3;

FIG. 5 is a top view of the electrode shown in FIGS. 3 and 4;

FIG. 6 is a top view of the electrode shown in FIG. 5 illustrating a lead wire electrical connection to the electrode;

FIG. 7 is a top view of the electrode shown in FIG. 5 illustrating an alligator clip electrical connection to the electrode;

FIG. 8 is a side view of the electrode shown in FIG. 4 illustrating an alternate, to that shown in FIG. 7, alligator clip electrical connection to the electrode;

DETAILED DESCRIPTION OF THE INVENTION

Figure 1:
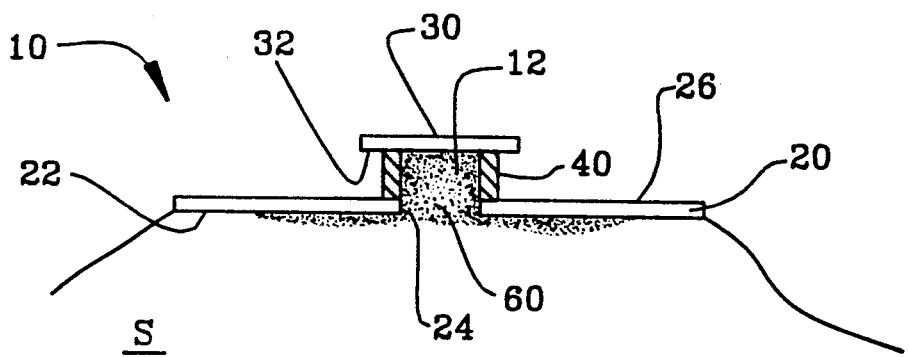
FIG. 1 is a cross-sectional view of a snapless, tabless, disposable medical electrode according to a first embodiment of the present invention.

Referring now to the drawing, like reference numerals refer to like elements throughout and the elements have been enlarged for clarity; in reality, the elements are very thin to form a low profile medical electrode. FIG. 1 shows a first embodiment of the snapless, tabless, disposable, low profile medical electrode 10 of the present invention. Electrode 10 is designed to contact the skin S of a patient for transmitting electrical signals between the skin and peripheral monitoring equipment 100 (see FIG. 6). Thus, electrode 10 can function to monitor or sense, stimulate, or diagnose.

In direct contact with skin S is an adhesive substrate 20. Substrate 20 may be formed of any suitable material, such as foam, tape, cloth, and the like. On its side (bottom) facing skin S, substrate 20 has a pressure sensitive adhesive layer 22 to promote adherence to skin S. Adhesive layer 22 may be made of any electrically conductive, pressure sensitive adhesive composition. The composition disclosed by Engel in U.S. Pat. No. 4,848,353 is suitable. Substrate 20 is preferably annular in shape and has a central, circular opening 24.

Substrate 20 is sufficiently flexible to move with skin S, minimizing the tendency, especially prevalent for inflexible electrodes, to "grip" the skin and cause irritation. Such flexibility also helps substrate 20 maintain electrical contact with skin S. In addition, substrate 20 may allow skin S to breath or release perspiration. Finally, substrate 20 is light weight. These characteristics—flexibility, breathability, light weight—of substrate 20 all prevent skin irritation and promote patient comfort.

An electrically conductive disk 30 is positioned over and projects above central opening 24 of substrate 20. To assure that electrode 10 has a low profile, disk 30 projects above substrate 20 the minimum distance required for attachment of lead wire 80 (see FIG. 6). Disk 30 is formed without either a tab or a snap. Disk 30 is symmetrical and preferably annular in shape. Disk 30 may be thermoformed of an electrically active form of carbon (e.g., graphite) or of a base coated with a conductive metal (e.g., Ag ink on a semi-rigid, nonconductive, thermoplastic material such as polyester, vinyl, or styrene) or of a conductive metal and metal salt (e.g., Ag/AgCl). Whatever its material of construction, disk 30 is substantially rigid to limit the susceptibility of electrode 10 to motion artifact and to provide for secure attachment.

Figure 2:
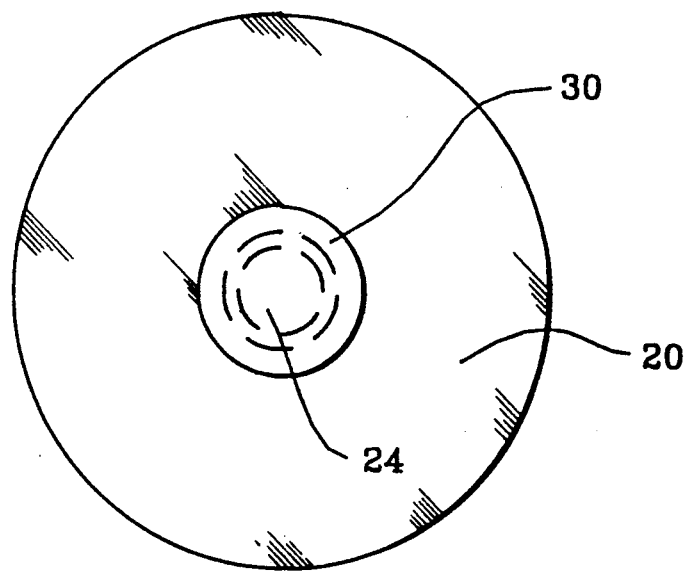
FIG. 2 is a top view of the electrode shown in FIG. 1.
Figure 9:
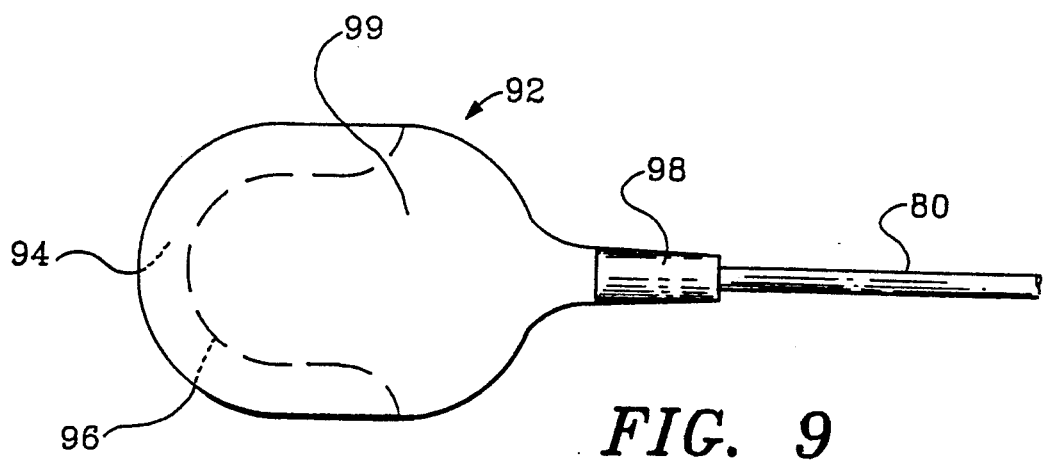
FIG. 9 is a top view of a lead wire adapter which can be used to provide electrical connection to both the first embodiment (shown in FIGS. 1 and 2) and the second embodiment (shown in FIGS. 3-5) of the medical electrode of the present invention.
Figure 10:
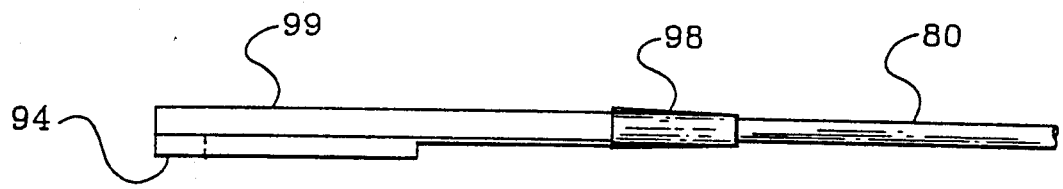
FIG. 10 is a side view of the lead wire adapter shown in FIG. 9.
Figure 11:
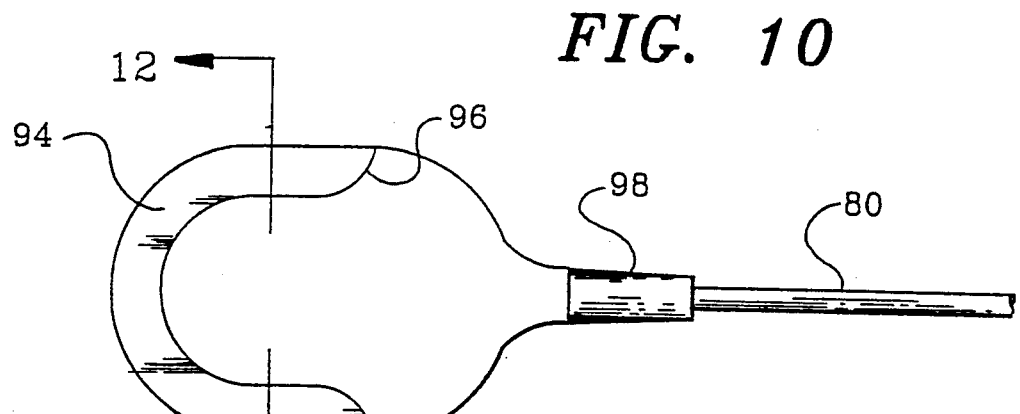
FIG. 11 is a top view of the lead wire adapter shown in FIG. 9 without a top layer.
Figure 12:
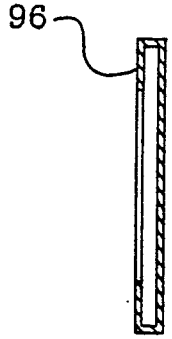
FIG. 12 is front view of the lead wire adapter taken along the section XII—XII of FIG. 11.

Two embodiments are shown in the Figures for connecting disk 30 to substrate 20. In the first embodiment, shown in FIGS. 1 and 2, an adhesive ring 40 is provided. The adhesive top of ring 40 contacts (or is integral with) the underside 32 of disk 30 while the adhesive base of ring 40 contacts the top 26 of substrate 20. Ring 40 is sufficiently adhesive to interconnect disk 30 with substrate 20. Ring 40 also has an annular, "donut" shape which tracks the perimeter of opening 24 in substrate 20 to form a cavity 12.

The second and preferred embodiment for connecting disk 30 to substrate 20 is shown in FIGS. 3-5. That embodiment eliminates adhesive ring 40. Instead, disk 30 has a hollow center portion 34 which engages opening 24 of substrate 20. An ultrasonic bond 50 is formed around the perimeter of disk 30 between disk 30 and substrate 20. Consequently, a cavity 12 is formed. Disk 30 is preferably saucer-like in configuration to reduce artifact and to facilitate construction.

A conductive medium 60 such an adhesive, electrolytic gel substantially fills opening 24 of substrate 20 and, hence, cavity 12 formed between disk 30 and substrate 20 in either embodiment. Medium 60 also contacts skin S and may cover a portion of adhesive layer 22 of substrate 20. Thus, medium 60 is in electrical contact with skin S, substrate 20, and disk 30. Medium 60 is preferably a hydrogel: a copolymer of acrylic acid and hydroxyethylmethacrylic acid with a humectant (glycerin). The amount of acrylic is controlled carefully to assure adhesion by the gel. The gel has a low Cl content (about one percent) to decrease skin irritation and to promote patient comfort. Moreover, the gel absorbs moisture to ensure consistent contact with skin S.

To prevent undesirable sticking between electrode 10 and various objects before electrode 10 is to be used, a release liner 70 is provided to cover conducting medium 60 and adhesive layer 22 of substrate 20. Liner 70 is removed just before electrode 10 is applied to skin S, thereby exposing medium 60 and adhesive layer 22 of substrate 20.

A lead wire 80 is provided to electrically connect electrode 10 to an external monitor 100. Lead wire 80 is attached on a first end to disk 30 of electrode 10. Attachment may be achieved by any one of the various techniques known in the art. For example, lead wire 80 may have a loop or hook which engages disk 30 (see FIG. 6). Alternatively, lead wire 80 may be attached to a spring or alligator clip 90 which, in turn, is attached to disk 30. Clip 90 can be any of a number of known configurations. One configuration suitable for clip 90 is shown in FIGS. 7 and 8. Note that, as shown in FIG. 7, clip 90 may be positioned on its side or, as shown in FIG. 8, in an upright position. The former configuration advantageously reduces the profile of the clip-electrode assembly.

A lead wire adapter 92 suitable for electrically connecting lead wire 80 to electrode 10 is shown in FIGS. 9-12. Lead wire 80 is attached, preferably by welding, to a thin conducting plate 94. A stress relief component 98 may be provided to assure attachment between lead wire 80 and conducting plate 94; stress relief component 98 may be made of molded rubber or plastic. Conducting plate 94 is provided with a cutout 96, preferably in the shape of a keyhole. To electrically connect lead wire 80 to electrode 10 using lead wire adapter 92, lead wire adapter 92, with lead wire 80 secured, is placed over disk 30 and pulled into engagement (electrical contact) with disk 30.

A top layer 99 may be applied over conducting plate 94 to protect conducting plate 94 and to prevent inadvertent contact by external objects with conducting plate 94. Top layer 99 may be made of plastic material.

The second end of lead wire 80, opposite the first end connected to disk 30, is adapted for connection to monitor 100. Accordingly, the second end of lead wire 80 may have a jack 82. Lead wire 80 is made of a durable, high-flex material; offers a low profile; and is reusable.

The first end (attached to disk 30) and second end (attached to monitor 100) of lead wire 80 can be attached to and detached from their respective components quickly and easily. Like existing snap electrodes, the design of electrode 10 allows for easy attachment and detachment (to and from the patient) without concern for a specific orientation. Unlike many existing electrodes, however, attachment between electrode 10 and its lead wire 80 can be made without regard to orientation (i.e., attachment at any position around the 360-degree periphery of electrode 10 is possible). Moreover, lead wire 80 can rotate even when attached to electrode 10. Attachment and detachment of electrode 10 to and from the patient, and of lead wire 80 to and from electrode 10, are sufficiently simple that they can be done even in the dark of a hospital room or a dimly lit operating room.

Electrode 10 is easy to use and especially to connect and disconnect. Unlike many existing electrodes, it is not at all cumbersome. Of special importance is the low profile, on the order of one-sixteenth of an inch, of electrode 10. The unique design of electrode 10 minimizes manufacturing costs yet meets all of the structural requirements of the market. Functionally, electrode 10 provides a good quality trace, of consistent accuracy, substantially all of the time. Electrode 10 limits the risk that active patients will cause motion artifact; a reduction in artifact saves the time and expense of re-running tests and may save a life.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. A snapless, tabless, disposable medical electrode having a low profile for transmitting electrical signals between the skin of a patient and external monitoring equipment, said electrode comprising:
   an adhesive substrate having a top, a central opening and a pressure sensitive adhesive layer on its bottom; said bottom for facing the patient;
   an electrically conductive disk having an underside and formed without a tab and without a snap and positioned over and projecting above said central opening of said substrate by a height of less than about one-sixteenth of an inch;
   a conductive electrolytic gel substantially filling said opening of said substrate and adapted to electrically contact the skin of the patient, said substrate, and said disk;
   means for securing said disk to said substrate;
   a lead wire for connecting said disk to the external monitoring equipment;
   means for attaching said lead wire to said disk without regard to orientation; and
   a release liner covering said bottom of said substrate and said conductive electrolytic gel before the electrode is secured to the skin of the patient.

2. A snapless, tabless, disposable medical electrode as claimed in claim 1 wherein the material of said substrate is chosen from the group consisting of foam, tape, and cloth.

3. A snapless, tabless, disposable medical electrode as claimed in claim 2 wherein said substrate is annular in shape and said central opening of said substrate is circular.

4. A snapless, tabless, disposable medical electrode as claimed in claim 3 wherein said substrate is flexible, breathable, and light weight.

5. A snapless, tabless, disposable medical electrode as claimed in claim 1 wherein said disk is annular and substantially rigid.

6. A snapless, tabless, disposable medical electrode as claimed in claim 5 wherein the material of said disk is chosen from the group consisting of an electrically conductive form of carbon; a non-conductive, thermoplastic base coated with a conductive metal; and a conductive metal and metal salt.

7. A snapless, tabless, disposable medical electrode as claimed in claim 6 wherein the material of said disk is graphite.

8. A snapless, tabless, disposable medical electrode as claimed in claim 6 wherein the material of said disk is silver ink coated on a non-conductive, thermoplastic base.

9. A snapless, tabless, disposable medical electrode as claimed in claim 6 wherein the material of said disk is silver/silver chloride.

10. A snapless, tabless, disposable medical electrode as claimed in claim 1 wherein said conductive gel is a copolymer hydrogel of acrylic acid and hydroxethylmethacrylic acid with a humectant.

11. A snapless, tabless, disposable medical electrode as claimed in claim 1 wherein said securing means includes an adhesive ring having a top and a base, said top attached to the underside of said disk and said base attached to the top of said substrate.

12. A snapless, tabless, disposable medical electrode as claimed in claim 11 wherein said adhesive ring tracks the perimeter of said central opening in said substrate to form a cavity substantially filled with said conductive electrolytic gel.

13. A snapless, tabless, disposable medical electrode as claimed in claim 13 wherein said securing means includes an ultrasonic bond formed around the perimeter of said disk between said disk and said substrate to form a cavity substantially filled with said conductive gel.

14. A snapless, tabless, disposable medical electrode as claimed in claim 13 wherein said disk has a hollow center portion which engages said central opening of said substrate and a saucer-like configuration.

15. A snapless, tabless, disposable medical electrode having a low profile for transmitting electrical signals between the skin of a patient and external monitoring equipment, said electrode comprising:
   a flexible, breathable and light weight adhesive substrate having a top, a central opening and a pressure sensitive adhesive layer on its bottom, said bottom for facing the patient;
   an electrically conductive, substantially rigid disk having an underside and formed without a tab and without a snap, said disk positioned over and projecting above said central opening of said substrate by a height of less than about one-sixteenth of an inch;
   a conductive electrolytic gel substantially filling said opening of said substrate and
   a release liner covering said bottom of said substrate and said conductive electrolytic gel before the electrode is secured to the skin of the patient.

16. A snapless, tabless, disposable medical electrode as claimed in claim 15 wherein said disk and said substrate are annular.

17. A snapless, tabless, disposable medical electrode as claimed in claim 16 wherein said adhesive ring tracks the perimeter of said central opening in said substrate to form a cavity substantially filled with said conductive electrolytic gel.

18. A snapless, tabless, disposable medical electrode having a low profile for transmitting electrical signals between the skin of a patient and external monitoring equipment, said electrode comprising:
   a flexible, breathable and light weight adhesive substrate having a top, a central opening and a pressure sensitive adhesive layer on its bottom, said bottom for facing the patient;
   an electrically conductive, substantially rigid disk formed without a tab and without a snap, said disk positioned over said central opening of said substrate;
   a conductive electrolytic gel substantially filling said opening of said substrate and adapted to electrically contact the skin of the patient, said substrate, and said disk;
   an ultrasonic bond formed around the perimeter of said disk between said disk and said substrate for securing said disk to said substrate and forming a cavity substantially filled with said conductive gel;
   a lead wire for connecting said disk to the external monitoring equipment, said disk projecting above said substrate the minimum distance required to attach said lead wire to said disk;
   means for attaching said lead wire to said disk without regard to orientation; and
   a release liner covering said bottom of said substrate and said conductive electrolytic gel before the electrode is secured to the skin of the patient.

19. A snapless, tabless, disposable medical electrode as claimed in claim 18 wherein said disk and said substrate are annular.

20. A snapless, tabless, disposable medical electrode as claimed in claim 19 wherein said disk has a hollow center portion which engages said central opening of said substrate and a saucer-like configuration.

21. A snapless, tabless, disposable medical electrode as claimed in claim 18 wherein said conductive gel is a copolymer hydrogel of acrylic acid and hydroxyethylmethacrylic acid with a humectant.

* * * * *